United States Patent [19]

Peet et al.

[11] Patent Number: 4,526,890
[45] Date of Patent: Jul. 2, 1985

[54] 3,6,7,8-SUBSTITUTED-S-TRIAZOLO[4,3-B]PYRIDAZINES AS BRONCHODILATORS

[75] Inventors: Norton P. Peet; Shyam Sunder, both of Indianapolis, Ind.

[73] Assignee: The Dow Chemical Company, Midland, Mich.

[21] Appl. No.: 251,794

[22] Filed: Apr. 7, 1981

Related U.S. Application Data

[63] Continuation of Ser. No. 89,071, Oct. 29, 1979, abandoned, which is a continuation-in-part of Ser. No. 44,876, Jun. 4, 1979, abandoned, which is a continuation of Ser. No. 889,771, Mar. 24, 1978, abandoned, which is a continuation of Ser. No. 714,738, Aug. 16, 1976, abandoned, which is a continuation of Ser. No. 574,056, May 2, 1975, abandoned.

[51] Int. Cl.³ .............. C07D 487/04; A61K 31/495; A61K 31/535; A61K 31/55
[52] U.S. Cl. ................... 514/248; 544/115; 544/118; 544/233; 544/234; 544/236
[58] Field of Search .......... 260/243.3; 544/115, 544/118, 233, 234, 236; 424/248.4, 250

[56] References Cited

U.S. PATENT DOCUMENTS

| 3,079,392 | 2/1963 | Pesson | 544/236 |
| 3,096,329 | 7/1963 | Stedl | 544/236 |
| 3,483,193 | 12/1969 | Gall | 544/236 |
| 3,708,484 | 1/1973 | Anderson | 544/236 |
| 3,915,968 | 10/1975 | Bellasio | 544/236 |
| 4,016,162 | 4/1977 | Bellasio | 544/236 |
| 4,112,095 | 9/1978 | Allen, Jr. | 544/236 |
| 4,136,182 | 1/1979 | Lewis et al. | 544/236 |

FOREIGN PATENT DOCUMENTS 1248409  3/1961  France .
51-95036  8/1976  Japan .

OTHER PUBLICATIONS

Fracaville et al., J. Het. Chem. 8, 4–5 (1971).
Lundina et al., Chem. Abs. 67, 21884q (196).
Pollak, *Jetrahedron* 22, 2073–2079 (1966).
Pasu, J. Chem. Soc. 1963, 5660.
Davies et al., Nature New Biology 234, 50 (1971).
Yurugi et al., Chem. Abs. 80, 37073d.
Twomey, Proc. Royal Irish Acad. 74B, 37–52 (1974).
Szilagyi et al., *Chem. Abs.* 92, 163919v.
Goodman & Gilman, "The Pharmucological Basis of Therapeutics", 1980, pp. 91–94, 144–149, 611–614.

*Primary Examiner*—Mark L. Berch
*Attorney, Agent, or Firm*—John J. Kolano; Maynard R. Johnson; Gary D. Street

[57]         ABSTRACT 3,6,7,8-Substituted-s-triazolo-pyridazine compounds such as 7,8-dimethyl-6-morpholino-3-methyl-s-triazolo[4,3-b]pyridazine or 7,8-dimethyl-6-(1-pyrrolidinyl)-3-(isopropyl)-s-triazolo-[4,3-b]pyridazine are prepared by the reaction of a carboxylic acid with a substituted 3-hydrazino-6-halo-pyridazine followed by the reaction of the resulting 6-halotriazolopyridazine with a corresponding base. The compounds have pharmacological activity as bronchodilators.

22 Claims, No Drawings

3,6,7,8-SUBSTITUTED-S-TRIAZOLO[4,3-B]PYRIDAZINES AS BRONCHODILATORS

This is a continuation of application Ser. No. 089,071, filed Oct. 29, 1979, abandoned, which in turn is a continuation-in-part of our application Ser. No. 044,876, filed June 4, 1979, abandoned, which is a continuation of application Ser. No. 889,771, filed Mar. 24, 1978, (now abandoned) which was in turn a continuation of application Ser. No. 714,738 filed Aug. 16, 1976, (now abandoned) which was in turn a continuation of application Ser. No. 574,056, filed May 2, 1975, and now abandoned.

BACKGROUND OF THE INVENTION

The compounds of the invention can be prepared by methods analogous to those described by Pollak et al., Tetrahedron 22, 2073 (1966); and Bellasio et al., U.S. Pat. Nos. 3,915,968 and 4,016,162. Other methods are described in Miller and Rose, J. Chem. Soc. 1963, 5642: Basu and Rose, J. Chem. Soc. 1963, 5660 (1963); and Davies et al., Nature New Biology, 234 50 (1971).

The compound 3-morpholino-6-methyl-8-phenyl-s-triazolo[4,3-b]pyridazine was described by Yurugi et al., Takeda Kenkyusho 32 (2), 111–117 (1973). Other morpholino triazolopyridazines are described in French Pat. No. 1248409 and in Chemical Abstracts, 67 21884 g.

SUMMARY OF THE INVENTION

The present invention relates to new pharmacologically active heterocyclic compounds. More particularly, the invention relates to 3,6,7,8-substituted s-triazolo[4,3-b]pyridazines corresponding to the formula

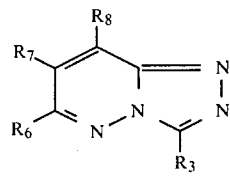

wherein $R_3$ represents hydrogen or loweralkyl. $R_6$ represents amino, loweralkylamino, diloweralkylamino, or heterocyclic amino or lower alkyl substituted heterocyclic amino, wherein the heterocyclic moiety forms a 5, 6 or 7 membered ring, having one or two ring nitrogen atoms and zero or one ring sulfur or oxygen atom; and wherein $R_7$ represents loweralkyl; wherein $R_8$ represents hydrogen or loweralkyl; and $R_7$ and $R_8$ taken together independently represent polymethylene or substituted polymethylene of 3 or 4 methylene units, e.g., $-CH_2-(CH_2)_n-$ wherein n is 2 or 3 substituted by loweralkyl, or methano or ethano bridges; and to pharmacologically acceptable salts of said compounds. The compounds wherein $R_7$ and $R_8$ are polymethylene or substituted polymethylene having four methylene units can be named either as s-triazolo[4,3-b]pyridazines or as 7,8,9,10-tetrahydro(1,2,4)triazolo[3,4-a]phthalazines. When so named, the 7,8,9 and 10 positions refer to the carbons of the tetramethylene group attached to the pyridazine residue. A preferred group of such compounds are those corresponding to Formula I in which $R_7$ and $R_8$, taken together are polymethylene or bridged polymethylene, said bridged polymethylene compounds corresponding to the formula

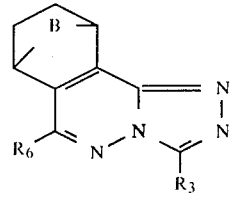

wherein $R_3$ and $R_6$ have the above significance, and B represents methylene or ethylene. Compounds of Formula II can be named as substituted triazolopyridazines or as tetrahydrotriazolophthalazines.

In the present specification and claims the terms "loweralkyl" and "lower alkoxy" refer to "loweralkyl" or "lower alkoxy" of one, two, three or four carbon atoms; and "halo" refers to fluoro, chloro or bromo. It is understood that the invention is inclusive of subgroups of compounds of the above formula, for example, those wherein $R_3$ is hydrogen; those wherein $R_3$ and $R_8$ are both hydrogen; those wherein $R_3$ represents hydrogen, methyl, ethyl or propyl; those wherein $R_6$ is pyrrolidino; those wherein $R_7$ and $R_8$ are substituted polymethylene substituted by loweralkyl, methano or ethano, those wherein $R_6$ is piperidino; those wherein $R_6$ is morpholino or thiamorpholino; those wherein $R_6$ is amino; those wherein $R_6$ is azepinyl or diazepinyl; or those wherein $R_6$ is N-methyl piperazino; those wherein $R_7$ and $R_8$ are polymethylene; those wherein $R_7$ and $R_8$ are substituted polymethylene, substituted with methano, etc. Such subgroups are apparent from the above description and the following specification; and further listing is omitted for the sake of brevity. Preferred groups of compounds comprise those wherein the loweralkyl is methyl; those wherein $R_3$ is hydrogen; those wherein $R_6$ is pyrrolidino, piperidino; 2-methylpyrrolidino, hexahydro-1H-azepin-1-yl, or 4-methyl-hexahydro-1H-1,4-diazepin-1-yl; those wherein $R_3$ is hydrogen or methyl; and those wherein $R_7$ and $R_8$ are polymethylene, with or without a methano or ethano bridge.

The 3,6,7,8-substituted-s-triazolo[4,3-b]pyridazine compounds corresponding to the above formulae and their pharmacologically acceptable salts have useful biological activity as bronchodilators and also have a desirably low toxicity and freedom from undesirable side effects at dosages consistent with good bronchodilator activity.

Some triazolopyridazines are known to have different properties. For example, 6-methyl-3-(4-morpholinyl)-8-phenyl-s-triazolo[4,3-b]pyridazine, rather than blocking histamine-induced bronchoconstriction, has been found to potentiate bronchoconstriction. The compound 6-morpholino-3-phenyl-s-triazolo[4,3-b]pyridazine, although a potent bronchodilator with a high $LD_{50}$ (low toxicity), has been found to produce audiogenic convulsions in laboratory animals at relatively low dosages. See, U.S. Pat. No. 4,136,182.

The triazolopyridazine compounds are crystalline solids which can be readily formulated in aqueous or alcoholic liquids. In general, the free base compounds are readily soluble in aqueous liquids, and the triazolopyridazine compounds are conveniently employed in either free base or salt form.

In practicing the method an effective bronchodilating amount of one or more substituted triazolopyridazine is administered internally to a mammal in need thereof by a route effective to bring the compound into contact with the bronchial and tracheal tissues of the mammal. Administration can be carried out either by a parenteral route, such as by intravenous, intraperitoneal, or intramuscular injection, or by introduction into the gastrointestinal tract via oral or rectal administration, for example, in order to bring about such contact via the blood stream, or by intratracheal administration, by inhalation of a solution in the form of a spray, for example.

The effective bronchodilating amount of the compound, that is, the amount of the substituted triazolopyridazine sufficient to inhibit or alleviate bronchial spasm depends on various factors such as the size, type and age of the animal to be treated, the particular triazolopyridazine or pharmacologically-acceptable salt employed, the route and frequency of administration, the severity of spasm (if any) and the causative agent involved, and the time of administration. In particular cases, the dosage to be administered can be ascertained by conventional range finding techniques, for example, by observing the bronchodilator activity produced at different dosage rates. Good results can be obtained when the compound is administered at dosage rates from about 1 to about 3, to about 10 to about 50 milligrams of substituted triazolopyridiazine compound per kilogram of animal body weight. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are preferred and the active triazolopyridiazine compound can be formulated in conventional timed release capsule or tablet formulations.

Some of the compounds can produce audiogenic convulsant side effects at dosages which, though much higher than the effective dose for bronchodilation, are still below a toxic dosage. Bronchodilator activity can be obtained at high, but non-toxic dosages at which additional factors could promote undesirable convulsant side effects, by eliminating other factors contributing to audiogenic convulsions. However, it is preferable to employ the compounds at effective dosages substantially below the audiogenic convulsant dosage, e.g. at one third, to one fifth, one-tenth or less of the audiogenic convulsant dosage. The audiogenic convulsant dosage, (dosage producing audiogenic convulsions) can be determined in known procedures, as described for example in U.S. Pat. No. 4,136,182.

In practicing the method of the invention, the active ingredient is preferably incorporated in a composition comprising a pharmaceutical carrier and from about 5 to about 90 percent by weight of the substituted triazolopyridazine compound or a pharmacologically-acceptable salt thereof. The term "pharmaceutical carrier" refers to known pharmaceutical excipients useful in formulating pharmacologically-active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions, and can contain suitable excipients known to be useful in the preparation of the particular type of composition desired. Suitable pharmaceutical carriers and formulation techniques are found in standard texts, such as Remington's Pharmaceutical Sciences, Mack Publishing Co., Easton, Pa.

As employed herein, the phrase "pharmacologically acceptable salt" refers to salts of the substituted triazolopyridazines, the anions of which are relatively nontoxic and innocuous to mammals at dosages consistent with good biological activity so that side effects ascribable to the anions do not vitiate the beneficial effects of the triazolopyridazine compounds. Suitable pharmacologically acceptable salts can be prepared by conventional procedures such as dissolving the free base compound in an inert organic solvent such as ether and treating the resulting solution with an excess ether solution of a suitable pharmacologically acceptable acid such as hydrochloric acid, or hydrobromic acid.

For the sake of brevity, such compounds will be hereinafter referred to simply as "triazolopyridazines".

The compounds of the invention are typically prepared by the reaction of a 3-halo-6-hydrazinopyridazine of formula III with a substituted carboxyl compound of formula IV

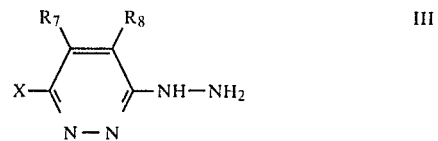

wherein $R_3$, $R_7$ and $R_8$ have the above significance and wherein X is halo, followed by reacting the resulting 6-halo-triazolopyridazine with the corresponding $R_6$ heterocyclic base.

Thus, the compounds of the invention can be prepared by first reacting a 3-chloro-6-hydrazinopyridazine with an appropriate acid of formula IV. This reaction proceeds when the reactants are contacted and mixed, preferably at the boiling temperature of the reaction mixture under reflux. The first step of the reaction is preferably carried out in an excess of the acid, the excess acid serving as reaction medium. The 6-halo-triazolopyridazine product can be recovered from the reaction mixture by evaporation to remove the excess acid reaction medium and can be purified by conventional procedures such as recrystallization and washing.

The substituted 6-halo-triazolopyridazine is then reacted with excess (e.g. at least two fold on a molar basis) of the $R_6$ base. The reaction is preferably carried out at the boiling temperature under reflux, using excess $R_6$ base or an inert organic solvent such as methanol, ethanol or isopropanol as a medium. The product is recovered by conventional procedures such as concentration under reduced pressure.

As an alternative procedure, the $R_6$ base can be reacted with a 3,6-dihalo-4,5-substituted pyridazine, and the product reacted with lower alkanoyl hydrazide such as formyl hydrazide or acetyl hydrazide to prepare the substituted triazolopyridazine.

The starting materials for the above method can be prepared by procedures which are known. The necessary pyridazines for the method above are obtained by reacting the appropriate 3,6-dihalo-4,5-substituted pyridazine with hydrazine hydrate.

The following examples illustrate the invention.

EXAMPLE 1

13.4 Grams (0.0845 mole) of 3-chloro-4-methyl-6-hydrazinopyridazine are dissolved in 100 milliliters of aqueous 88 percent formic acid. The mixture is heated at the boiling temperature under reflux for 2 hours. The mixture is evaporated under reduced pressure and the 7-methyl-6-chloro-s-triazolo[4,3-b]pyridazine intermediate product is obtained as a residue. The residue is triturated with diethyl ether, and found to melt at a temperature of 157.5°–158° C.

7.8 Grams (0.0462 mole) of the 6-chloro-7-methyl-s-triazolo[4,3-b]pyridazine is mixed with 7.86 grams (0.0924 mole) of piperidine in 50 ml of ethanol. The mixture is heated at reflux temperature for 4 hours. The mixture is concentrated by evaporation and the residue of the reaction mixture is partitioned between aqueous sodium bicarbonate solution and methylene chloride. The methylene chloride layer is separated, dried over anhydrous sodium sulfate and evaporated to dryness under reduced pressure. The 7-methyl-6-piperidino-s-triazolo[4,3-b]pyridazine product is obtained as a residue from the evaporation. The product is recrystallized from hexane and found to melt at 78°–79° C. The structure of the product is confirmed by infrared spectroscopy, by nuclear magnetic resonance analysis, and by elemental analysis. (Calculated for $C_{11}H_{15}N_5$: C, 60.80; H, 6.96; N, 32.24. Found: C, 60.40; H, 6.98; N, 32.17.)

EXAMPLE 2

6-Chloro-3,7-dimethyl-s-triazolo[4,3-b]pyridazine (4.56 grams; 0.025 mol) and 4.36 grams (0.05 mol) of morpholine are mixed together in 20 ml ethanol and heated at the boiling temperature under reflux for 4 hours. After cooling, crystals are observed in the reaction vessel. The reaction mixture and crystals are partitioned between methylene chloride (50 ml) and water. The aqueous layer is extracted twice with methylene chloride and the combined methylene chloride layers are dried over anhydrous sodium sulfate. The dried methylene chloride solution is then evaporated to dryness under reduced pressure, and 5.68 grams of the 3,7-dimethyl-6-morpholino-s-triazolo[4,3-b]pyridazine product are obtained. The product is recrystallized twice from a benzene-hexane mixture. The product is found to melt at a temperature of 160°–174° C. Structure of the product is confirmed by infrared spectroscopy and by elemental analysis, and nuclear magnetic resonance analysis shows the presence of about 71 percent of the 3,7-dimethyl product with about 29 percent of the 3,8-dimethyl isomer.

The corresponding 6-piperidino compound is similarly obtained with about 30 percent of the 3,8-dimethyl isomer. The product melts at 102°–114° C.

EXAMPLE 3

6-Chloro-7-methyl-s-triazolo[4,3-b]pyridazine (2.4 grams; 0.014 mol) and excess pyrrolidone (about 0.028 mol) are mixed together in ethanol and heated under reflux overnight (about 18 hours). The reaction mixture is then evaporated and the residue is partitioned between methylene chloride and saturated aqueous sodium bicarbonate solution. The methylene chloride layer is separated, washed with water, dried with anhydrous sodium sulfate, and evaporated to dryness. The 7-methyl-6-pyrrolidino-s-triazolo[4,3-b]pyridazine product is crystallized from ethanol and observed to melt at 186°–187° C. Molecular weight calculated: 230.24, mass spectroscopy (70 eV) m/e 203.

7-Methyl-6-morpholino-s-triazolo[4,3-b]pyridazine is similarly prepared and found to melt at 172°–173° C. Calculated C, H, N: 54.78, 5.98, 31.95; Found C, H, N: 54.90, 5.76, 31.84.

EXAMPLE 4

7-Methyl-6-N-methylpiperazino-s-triazolo[4,3-b]pyridazine is similarly prepared. This product is found to melt at 169°–170° C. The product is found by elemental analysis to have carbon, hydrogen, and nitrogen contents of 56.8, 6.7 and 36.2 percent, respectively, as compared with the theoretical contents of 56.9, 6.9 and 36.2 percent, respectively, calculated for the named structure. Molecular weight, calculated: 232.2, by mass spectroscopy (70 eV) m/e 232.

EXAMPLE 5

1-Chloro-4-hydrazino-5,6,7,8-tetrahydro-5,8-methanophthalazine (25 grams; 0.12 mol) was mixed with 150 milliliters of formic acid and heated at the boiling temperature under reflux for 2 hours. The reaction mixture was concentrated by evaporation under reduced pressure and taken up in aqueous sodium bicarbonate. The resulting precipitate was collected by filtration, washed with water and dried in air. The 6-chloro-7,8,9,10-tetrahydro-7;10-methano[1,2,4]triazolo-[3,4-a]phthalazine product (21.6 grams, 82.5% yield) was found to melt at 155°–156° C., and at 157°–158° C. after recrystallization from a benzene-hexane mixture. The structure was confirmed by infrared spectroscopy, nuclear magnetic resonance analysis and elemental analysis. (Calculated for $C_{10}H_9ClN_4$: C, 54.42; H, 4.11; N, 25.39. Found: C, 54.40; H, 4.12; N, 25.20). This 6-chloro compound (6.5 grams, 0.029 mol) was mixed with 25 milliliters of N-methylpiperazine, and the mixture heated at boiling under reflux for 6 hours. The mixture was concentrated by evaporation under reduced pressure, then partitioned between methylene chloride and water. The organic layer was separated, dried over sodium sulfate and concentrated to obtain the 7,8,9,10-tetrahydro-6-[4-methyl-1-piperazinyl)-7,10-methano(1,2,4)triazolo[3,4-a]phthalazine product. After recrystallization from benzene/hexane, 6.6 grams (79 percent yield) of the product were obtained, with a melting point of 172°–173° C. Structure was confirmed by infrared and nuclear magnetic resonance analysis, and by elemental analysis. (Calculated for $C_{15}H_{20}N_6$: C, 63.35; H, 7.09; N, 29.56. Found: C, 63.30; H, 7.05; N, 29.33.)

EXAMPLE 6

In a procedure similar to that of Example 5, 1-chloro-4-hydrazino-5,6,7,8-tetrahydro-5,8-methanophthalazine (25.0 grams, 0.119 mol) was mixed with 150 milliliters of acetic acid, and the mixture was heated at the boiling temperature under reflux for two hours. The reaction mixture was concentrated and the residue taken up in aqueous sodium bicarbonate. The resulting precipitate was collected, washed with water and air-dried to yield 23.4 grams (84 percent yield) of 6-chloro-7,8,9,10-tetrahydro-3-methyl-7,10-methano(1,2,4)triazolo[3,4-a]phthalazine. After recrystallization from benzene-hexane this product melted at 137°–138° C. Infrared spectroscopy and elemental analysis were consistent with the named structure.

The 6-chloro-7,8,9,10-tetrahydro-3-methyl-7,10-methano(1,2,4)triazolo[3,4-a]phthalazine (4.5 grams, 0.019 mol) was mixed with 25 milliliters of morpholine and the mixture heated at boiling under reflux for eight hours. The reaction mixture was concentrated and partitioned between methylene chloride and water. The organic layer was collected, dried over sodium sulfate and evaporated to dryness to yield 4.4 grams (80.6% yield) of 7,8,9,10-tetrahydro-3-methyl-6-(4-morpholinyl)-7,10-methano(1,2,4)triazolo[3,4-a]phthalazine. After recrystallization from benzene-hexane the product was found to melt at 166°–168° C. Infrared analysis and nuclear magnetic resonance analysis confirmed the assigned structure, as did elemental analysis. Calculated for $C_{15}H_{19}N_5O$: C, 63.14; H, 6.71; N, 24.55. Found: C, 63.20; H, 6.71; N, 24.32.

EXAMPLES 7–14

In a procedure similar to those of the preceding examples, the following compounds are prepared. In each case the $R_7$ and $R_8$ substituents of Formula I, taken together are 1,3-cyclopentylene, and the compounds thus correspond to the general formula

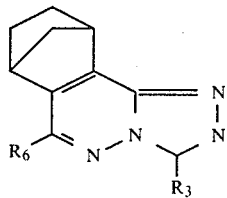

wherein $R_3$ and $R_6$ are as defined above with respect to Formula I.

heated at the boiling temperature under reflux for 2 hours, then evaporated to dryness. The residue was triturated with saturated aqueous sodium bicarbonate. The resulting white solid was collected, washed with water and air dried to yield 23.0 grams (88% yield) of 6-chloro-7,8,9,10-tetrahydro-7,10-ethano(1,2,4)-triazolo[3,4-a]phthalazine, melting at 137°–140° C. After recrystallization from a mixture of benzene and hexane the purified product melted at 140.5°–141° C. Infrared spectroscopy and elemental analysis confirmed the designated structure.

In substantially the same procedure, using acetic acid instead of formic acid, 23.8 grams of 6-chloro-7,8,9,10-tetrahydro-3-methyl-7,10-ethano(1,2,4)triazolo[3,4-a]phthalazine was produced (86 percent yield). Melting point 178°–179° C. after recrystallization from benzene-hexane.

Using 5 to 10 grams of one of the two above substituted 6-chloro-triazolopyridazines and 50 milliliters of the appropriate amine $R_6$ reactant, the following compounds were prepared. Reaction mixtures were heated at reflux for about 2 hours. Reaction mixtures were then concentrated and partitioned between water and methylene chloride. The organic layers were dried and concentrated. In each case, the $R_7$ and $R_8$ substituent is 1,4-cyclohexylene, so the compounds are nameable as 7,8,9,10-tetrahydro-3,6-substituted-7,10-ethano-1,2,4-triazolo[3,4-a]phthalazines, corresponding to the general formula

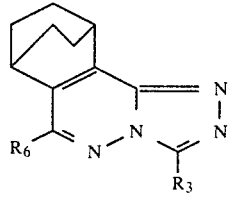

wherein $R_3$ and $R_6$ are as defined above with respect to Formula I.

| Compound | $R_3$ | $R_6$ | Melting Point °C. | Recrystallization Solvent | Yield (Percent) |
|---|---|---|---|---|---|
| 7 | H | 1-Pyrrolidinyl | 189–191 | benzene-hexane | 92 |
| 8 | H | 1-Piperdinyl | 122–122.5 | benzene-hexane | 85 |
| 9 | H | 4-Morpholinyl | 201–203 | benzene-hexane | 67 |
| 10 | $CH_3$ | 1-Pyrrolidinyl | 166–168 | benzene-hexane | 78 |
| 11 | $CH_3$ | 1-Piperdinyl | 125.5–127 | benzene-hexane | 83 |
| 12* | H | 4-Methyl-1-piperazinyl (dihydrochloride) | 278–280 | ethanol | 91.6 |
| 13 | $CH_3$ | 4-Methyl-1-piperazinyl | 129–130 | benzene-hexane | 64.1 |
| 14* | $CH_3$ | 4-Methyl-1-piperazinyl (dihydrochloride) | 271–273 | ethanol-ether | 97.4 |

*Produced by dissolving the free base in benzene and saturating the benzene solution with HCl gas to precipitate the dihydrochloride salts.

EXAMPLES 15–23

1-Chloro-4-hydrazino-5,6,7,8-tetrahydro-5,8-ethanophthalazine (2.5 grams, 0.111 mol) was mixed with 150 milliliters of formic acid. The mixture was

| Compound | $R_3$ | $R_6$ | Melting Point °C. | Recrystallization Solvent | Yield (Percent) |
|---|---|---|---|---|---|
| 15 | H | 1-Pyrrolidinyl | 181–183 | benzene-hexane | 97 |
| 16 | H | 1-Piperdinyl | 141–143 | benzene-hexane | 85 |
| 17 | H | 4-Morpholinyl | 220–221 | benzene-hexane | 71 |
| 18 | $CH_3$ | 1-Pyrrolidinyl | 206–208 | benzene-hexane | 87 |
| 19 | $CH_3$ | 1-Piperdinyl | 207–209 | benzene-hexane | 54 |
| 20 | $CH_3$ | 4-Morpholinyl | 217–218 | benzene-hexane | 83 |

-continued

| Compound | $R_3$ | $R_6$ | Melting Point °C. | Recrystallization Solvent | Yield (Percent) |
|---|---|---|---|---|---|
| 21 | H | 4-Methyl-1-piperazinyl | 214–215 | benzene | 69 |
| 22* | H | 4-Methyl-1-piperazinyl.2HCl | over 300 | ethanol-ether | 72.8 |
| 23 | $CH_3$ | 4-Methyl-1-piperazinyl (free base) | 218–220 | benzene-hexane | 60 |

*Produced by dissolving 2 grams of compound 21 in 50 milliliters of benzene and saturating the solution with hydrogen chloride gas. The resulting precipitate was collected and air-dried and the structure confirmed by infrared and elemental analysis. The dihydrochloride salt 22 was dissolved in water and the solution made basic with saturated sodium bicarbonate. The mixture was extracted with methylene chloride and the extract concentrated and scratched to a solid. The structure of the resulting free base compound 21 was confirmed by infrared analysis.

EXAMPLE 24

1-Chloro-4-hydrazino-5,6,7,8-tetrahydrophthalazine, also nameable as 3-chloro-4,5-tetramethylene-6-hydrazino pyridazine, (50 grams, 0.25 mol) was mixed with 250 milliliters of formic acid. The mixture was heated at the boiling temperature under reflux for 2 hours. The mixture was concentrated by evaporation under reduced pressure, and the oily residue mixed with saturated aqueous sodium bicarbonate solution. The resulting white solid was separated by filtration, washed with water and dried in air. The 6-chloro-7,8,9,10-tetrahydro(1,2,4)triazolo[3,4-a]phthalazine product was recrystallized from alcohol-hexane and found to melt at 124°–125° C. (Yield 42.4 grams, 81 percent). Elemental analysis confirmed the structure.

10.4 Grams (0.05 mol) of the 6-chloro-7,8,9,10-tetrahydro(1,2,4)triazolo[3,4-a]phthalazine were mixed with 8.53 grams (0.12 mol) pyrrolidine in 100 milliliters of ethanol. The mixture was heated at the boiling temperature under reflux for 10 hours, then concentrated by evaporation under reduced pressure until a solid residue was obtained. The solid was partitioned between methylene chloride and water; the organic layer was collected and the water layer extracted twice with methylene chloride. The methylene chloride layer and extracts were combined, dried over anhydrous sodium sulfate, filtered and evaporated under reduced pressure. The resulting colorless solid 6-(1-pyrrolidinyl)-7,8,9,10-tetrahydro(1,2,4)triazolo[3,4-a]phthalazine product was crystallized from ethanol and found to melt at 194°–195.5° C. 9 Grams of product were obtained, a 74 percent yield from this step. Elemental analysis confirmed the structure (Calculated for $C_{13}H_{17}N_5$: C, 64.17; H, 7.04; N, 28.79. Found: C, 64.4; H, 7.01; N, 28.83.) The product is also named as 6-pyrrolidino-7,8-tetramethylene-s-triazolo[4,3-b]pyridazine.

EXAMPLE 25

In a similar procedure, 6-piperidino-7,8-tetramethylene-s-triazolo[4,3-b]pyridazine, also named as 6-piperidino-7,8,9,10-tetrahydro(1,2,4)triazolo[3,4-a]phthalazine, melting at 134.5°–135.5° C. was prepared.

EXAMPLE 26

In a procedure similar to those of the preceding examples, 40 grams of 3-chloro-4,5-dimethyl-6-hydrazinopyridazine and 200 milliliters of aqueous 80 percent formic acid were heated at reflux for 90 minutes to obtain 6-chloro-7,8-dimethyl-s-triazolo[4,3-b]pyridazine. This triazolopyridazine (9.18 grams, 0.05 mole) was mixed with 12.25 grams N-methylpiperazine in 80 milliliters of ethanol, and the mixture was heated at reflux for 3 hours. The product was recovered by evaporation, partitioning the oily residue between methylene chloride and water and evaporation of the organic layer. The resulting 6-(N-methylpiperazino)-7,8-dimethyl-s-triazolo[4,3-b]pyridazine was obtained as colorless crystals. Thin layer chromatography on silica gel developed with 90 percent chloroform: 10 percent methanol indicated the presence of triazolopyridazine intermediate in the product. The product was taken up in excess N-methylpiperazine and heated at reflux for 12 hours, followed by 2 hours of reflux in 20 milliliters of N-methylpiperazine. The resulting 6-(N-methylpiperazino)-7,8-dimethyl-s-triazolo[4,3-b]pyridazine was obtained as colorless crystals. Thin layer chromatography on silica gel developed with 90 percent chloroform: 10 percent methanol indicated the presence of triazolopyridazine intermediate in the product. The product was taken up in excess N-methylpiperazine and heated at reflux for 12 hours, followed by 2 hours of reflux in 20 milliliters of N-methylpiperazine. The resulting 6-(N-methylpiperazino)-7,8-dimethyl-s-triazolo[4,3-b]pyridazine was separated as before, crystallized from benzene-hexane and found to melt at 170°–172° C. (Calculated: C, 58.51; H, 7.37; N, 34.12. Found: C, 58.70; H, 7.27; N, 34.18.)

EXAMPLE 27

In a procedure similar to Example 26, 6-chloro-7,8,9,10-tetrahydro(1,2,4)triazolo[3,4-a]phthalazine (prepared as in Example 24) (10 grams, 0.048 mol) and 12.2 grams (0.122 mol) of N-methylpiperazine in 100 milliliters of ethanol were heated at reflux for 20 hours. Thin layer chromatography (TLC) showed the presence of unreacted phthalazine. The ethanol was evaporated, 50 milliliters of N-methylpiperazine were added and the mixture heated at reflux for 2 hours, after which TLC indicated the reaction to be complete. The mixture was concentrated, and partitioned between methylene chloride and water, and the residue from evaporation of the methylene chloride was recrystallized twice from a mixture of benzene and hexane, then once from hexane. The 6-(4-methyl-1-piperazinyl)-7,8-tetramethylene(1,2,4)triazolo[4,3-b]pyridazine product was found to melt at 160°–162° C. 12.45 Grams of the product were obtained (95 percent yield). The structure was confirmed by nuclear magnetic resonance analysis and infrared spectroscopy. (Calculated: C, 61.74; H, 7.40; N, 30.86. Found: C, 61.90; H, 7.35; N, 30.59). Nuclear magnetic resonance ($CDCl_3$); $\delta$9.84 (s, 1, CH); 3.4–3.0 (m,6); 2.8–2.5 (m,6) 2.38 (s, 3, $CH_3$); 2.1–1.7 (m, 4, $CH_2CH_2CH_2CH_2$). Melting point of monohydrochloride salt 265°–266° C.

In similar procedures, the following are prepared:
7,8-Dimethyl-6-pyrrolidino-s-triazolo[4,3-b]pyridazine, melting at 143°–144° C.;

6-Morpholino-7,8-tetramethylene-s-triazolo[4,3-b]pyridazine, also named as 6-morpholino-7,8,9,10-tetrahydro(1,2,4)triazolo[3,4-a]phthalazine, melting at 194°–196° C.;

6-Morpholino-7,8-dimethyl-s-triazolo[4,3-b]pyridazine, molecular weight 233.27, melting at 143°–145° C.;

6-Pyrrolidino-3,7-di-n-propyl-s-triazolo[4,3-b]pyridazine, molecular weight 275.39;

6-(2-Methylpiperidino)-7,8-tetramethylene-s-triazolo[4,3-b]pyridazine, melting at 84°–86°, molecular weight 299.41.

6-N-methylpiperazino-7-ethyl-s-triazolo[4,3-b]pyridazine, molecular weight 246.31;

6-Piperidino-7,8-trimethylene-s-triazolo[4,3-b]pyridazine, molecular weight 243.31;

6-Piperidino-3-methyl-7,8-tetramethylene-s-triazolo[4,3-b]pyridazine, melting at 144°–144.5° C.;

6-Pyrrolidino-3,7,8-trimethyl-s-triazolo[4,3-b]pyridazine, molecular weight 231.30;

6-Piperidino-3,7,8-trimethyl-s-triazolo[4,3-b]pyridazine, melting at 138°–139° C.;

6-Morpholino-3,7,8-trimethyl-s-triazolo[4,3-b]pyridazine, melting at 123°–124° C.;

6-Piperidino-7,8-dimethyl-s-triazolo[4,3-b]pyridazine, melting at 127°–128° C.;

6-Morpholino-3-methyl-7,8-tetramethylene-s-triazolo[4,3-b]pyridazine, melting at 189°–190° C.

EXAMPLE 29

6-Chloro-7,8,9,10-tetrahydro(1,2,4)triazolo[3,4-a]phthalazine (7.2 grams; 0.0345 mole) was mixed with 20 milliliters of hexamethylenimine and 100 milliliters of methanol. The mixture was heated at the boiling temperature under reflux for 30 hours, cooled and partitioned between methylene chloride and water. The methylene chloride layer was dried and evaporated to dryness. The residue was recrystallized from benzene-hexane to give the 6-(hexahydro-1H-azepin-1-yl)-7,8-tetramethylene(1,2,4)triazolo[4,3-b]pyridazine as colorless crystals, melting at 109° C. Elemental analysis: C, H, N calculated: 66.39; 7.80; 25.81; C, H, N found: 66.04; 7.42; 25.76. The above reaction was carried out without the methanol reaction medium, and the product was found to melt at 108°–109° C.

EXAMPLE 30

15.65 Grams of 6-chloro-7,8-tetramethylene(1,2,4)-triazolo[4,3-b]pyridazine and 35 milliliters of 2-methylpyrrolidine were mixed and heated under reflux for two hours. The reaction mixture was evaporated to dryness, and partitioned between methylene chloride and water. The methylene chloride layer was dried and evaporated to leave 12.5 grams (64.8% yield) of 6-(2-methylpyrrolidinyl)-7,8-tetramethylene(1,2,4)triazolo[4,3-b]pyridazine. The product was recrystallized from benzene-hexane and found to melt at 146°–147° C. C, H, N calculated: 65.34; 7.44; 27.22. C, H, N found: 65.5; 7.51; 27.36.

EXAMPLES 31–37

In procedures similar to those of Examples 29 and 30, the following 6-substituted-7,8-tetramethylene-s-triazolo[4,3-b]pyridazines were prepared. The compounds are identified below by the $R_6$ substituents; $R_7$ and $R_8$ being tetramethylene and $R_3$ being hydrogen.

| Example | $R_6$ | Yield (Percent) | Melting Point °C. |
|---|---|---|---|
| 31 | Methylamino | 86 | 155–156 |
| 32 | Dimethylamino | 71.7 | 153–154 |
| 33 | 3-Methylpiperidino | 100 | 99–102 |
| 34 | 4-Methylpiperidino | 100 | 152.5–154 |
| 35 | Hexahydro-4-methyl-1H—1,4-diazepin-1-yl | 63.3 | 135–136 |
| 36 | dihydrochloride salt of 35 | | 249–251 |
| 37 | Ethylamino | — | 250–251 |

EXAMPLES 38–44

In a similar procedure, the following compounds were prepared, in which $R_3$ is methyl, $R_7$ and $R_8$ are tetramethylene, and $R_6$ is identified below.

| Example | $R_6$ | Yield (Percent) | Melting Point °C. |
|---|---|---|---|
| 38 | Methylamino | 78.1 | 279–280 |
| 39 | Dimethylamino | 72.6 | 128–129 |
| 40 | 2-Methyl-1-pyrrolidinyl | 50 | 142 |
| 41 | 3-Methylpiperidino | 61 | 152–153 |
| 42 | 4-Methylpiperidino | 81.7 | 143–144 |
| 43 | 4-methyl-1-piperazinyl | 66.8 | 183 |
| 44 | Hexahydro-4-methyl-1H—1,4-diazepin-1-yl dihydrochloride | 56.6 / 56.9 | 114–115 / 240–241 |

EXAMPLES 45–53

A. A solution of 98.5 grams (0.496 mole) of 1-chloro-4-hydrazino-5,6,7,8-tetrahydrophthalazine in 300 milliliters of propionic acid was heated at reflux for 18 hours, then concentrated by evaporation to half the original volume. The solution was diluted with aqueous sodium carbonate until neutral (pH 7). The resulting precipitate was collected, air-dried at ambient temperature, then dried in a drying over to produce 105 grams (0.444 mol) of 6-chloro-3-ethyl-7,8,9,10-tetrahydro-1,2,4-triazolo[3,4-a]phthalazine, melting at 93°–94° C. (89.6% yield). Calculated for $C_{11}H_{13}ClN_4$: C, 55.81; H, 5.53; N, 23.67. Found: C, 56.00; H, 5.63; N, 23.87.

B. In a procedure similar to the foregoing examples, the 6-chlorotetramethylenetriazolopyridazine intermediate product was reacted with excess $R_6$ amine (more than two equivalents) at reflux. Reaction progress was monitored by thin layer chromatography on silica gel, developed with 9:1-chloroform:methanol, where the 6-chloro intermediate appeared as a fluorescent spot and the product was non fluorescent. After reaction was complete, the reaction mixtures were concentrated, and the residue partitioned between water and methylene chloride. The organic layer was dried with sodium sulfate, concentrated and the residue recrystallized from benzene-hexane. Salts were formed by dissolving the base in acetone and adding ethereal acid (hydrogen chloride). Using the above 6-chloro intermediate, the following were prepared, in which $R_3$ is ethyl, $R_7$ and $R_8$ are tetramethylene, and $R_6$ is identified below.

| Example | $R_6$ | Yield (Percent) | Melting Point °C. |
|---|---|---|---|
| 45 | Hexahydro-4-Methyl-1H—1,4-diazepin-1-yl | 44 | 95–96 |
| 46 | Dihydrochloride of 45* | 53 | 225–228 |

-continued

| Example | R₆ | Yield (Percent) | Melting Point °C. |
|---|---|---|---|
| 47 | Hexahydroazepin-1-yl | 28.2 | 104 |
| 48 | Morpholino | 62.0 | 170-171 |
| 49 | Piperidino | 57.8 | 135-136 |
| 50 | 2-Methylpyrrolidino | 55.2 | 152-153 |
| 51 | Pyrrolidino | 59.8 | 118-119 |
| 52 | 4-Methyl-1-piperazinyl | 67.8 | 172-173 |
| 53 | Dihydrochloride of 52** | 86.7 | 250-252 |

*Recrystallized from methanol-acetone
**Recrystallized from isopropanol

EXAMPLES 54–56

A. In a procedure similar to that of Example 45A, 98.5 grams of 1-chloro-4-hydrazino-5,6,7,8-tetrahydrophthalazine was heated at reflux in 300 milliliters of isobutyric acid. After 18 hours, excess isobutyric acid was distilled off and the residue neutralized with aqueous sodium bicarbonate. The resulting solid 6-chloro-7,8,9,10-tetrahydro-3-(1-methylethyl)-1,2,4-triazolo[3,4-a]-phthalazine was collected and air-dried to yield 100 grams (80.4 percent yield). After recrystallization from isopropanol the yield was 56.2 grams, melting at 67°–68° C.

B. Using the above 6-chloro intermediate product, and the procedure described in Example 45B and the preceding Examples, the following compounds were prepared, in which $R_3$ is isopropyl, $R_7$ and $R_8$ are tetramethylene, and $R_6$ is identified below:

| Example | R₆ | Yield (Percent) | Melting Point °C. |
|---|---|---|---|
| 54 | Hexahydro-4-methyl-1H—1,4-diazepin-1-yl | 55.9 | 62–63 |
| 55 | 2-Methyl-pyrrolidino | 44.5 | 129–130 |
| 56 | Pyrrolidino | 32.6 | 119–121 |

EXAMPLE 57

Bronchodilator activity of representative triazolopyridazine compounds of the invention is examined in the Konzett-Rossler guinea pig preparation according to accepted procedures. See Knozett and Rossler; Arch. f. Exp. Path. u. Pharmakol. 195: 71–74 (1940); Rosenthale and Dervinis, Arch. Int. Pharmacodyn. 172: 91–94 (1968). In this procedure an anesthetized guinea pig is artificially respired with a fixed volume of air. The volume of air is selected to slightly exceed the capacity of the guinea pig's lungs, and the excess air or "overflow" is measured. Test compounds are evaluated by administering a test compound intravenously 2 minutes prior to administration of an agonist compound (histamine, serotonin or acetylcholine) following 3 previous agonist doses resulting in relatively uniform (±10 percent) bronchoconstriction. When the bronchospasm resulting from administration of the agonist compound occurs, the animal's lungs can receive less air, and hence the "overflow" is measurably increased. When a test compound blocks the bronchoconstriction induced by administration of the agonist compound, the results can be expressed quantitatively as a percent blockade. This is calculated by dividing the "overflow" agonist response measured after administration of the test compound by the average of the 3 preceding agonist responses, multiplying by 100 and subtracting this value from 100 percent. The results can also be expressed in comparison to a known bronchodilator, such as aminophylline. In such procedure, comparative results are expressed as "percent aminophylline", calculated by expressing the percentage blockade produced by a test compound as a percentage of the average percent blockade produced by dosages of aminophylline administered to the same test animal employed for the test compound with the aminophylline observations preceding and following the evaluation of the test compound in that animal.

In representative operations with triazolopyridazine compounds of the invention, administered intravenously at a dosage rate of 3 milligrams of test compound per kilogram of animal body weight (except as otherwise indicated) and using aminophylline at a dosage rate of 10 milligrams per kilogram for comparison and histamine as the agonist, representative compounds gave excellent results in terms of percent blockade of histamine and percent of aminophylline.

7,8-Dimethyl-6-pyrrolidino-s-triazolo[4,3-b]-pyridazine, administered as an aqueous solution was found to give a 65 percent blockade of histamine, amounting to 67 percent of aminophylline activity.

In similar operations, the compound 6-pyrrolidino-7,8-tetramethylene-s-triazolo[4,3-b]pyridazine and the compound 6-morpholino-7,8-tetramethylene-s-triazolo[4,3-b]pyridazine gave 100 and 75 percent blockade of histamine, respectively, amounting to 105 and 113 percent of aminophylline activity. 3,7-Dimethyl-6-morpholino-s-triazolo[4,3-b]pyridazine, 6-(N-methylpiperazino)-7-methyl-s-triazolo[4,3-b]pyridazine, and 3,7-dimethyl-6-piperidino-s-triazolo[4,3-b]pyridazine gave average percent blockades of 61, 39 and 48 percent, respectively.

EXAMPLE 58

Audiogenic Convulsive Side Effects

Certain xanthine compounds, such as the known bronchodilator aminophylline, have central nervous system stimulant side effects which are difficult to detect in animal models which are satisfactory for evaluating other compounds. The interaction of sound with the convulsive threshold of drugs is a known phenomenon which can be used to evaluate such side effects. See, for example, Schlesinger et al., Life Science 4, 2345–2351 (1965), 7, 437–447 (1968) and 9 (I) 721–729 (1970); Buckholtz, Pharmacol. Biochem. and Bahavior 3, 65–68 (1975); and U.S. Pat. No. 4,136,182. In a procedure for pharmacological evaluation, the lowering of the convulsive threshold, or the lowering of the $LD_{50}$, by sound can be studied in mice.

In the test operations, mice are administered a test compound by intraperitoneal injection at various dosages, and the number of mice showing tonic convulsions and the number of fatalities occurring within 30 minutes is recorded. The $ED_{50}$ for tonic convulsions, and the 30 minute $LD_{50}$ are then determined. These operations are carried out in standard laboratory cages with mice that have become acclimated to the laboratory.

The surviving mice are then also exposed to sound about 30 minutes after dosing. The sound exposure is carried out by placing the mice in a sound insulated cage with a bell which emits 120 decibels of sound, and activating the bell for two minutes. The number of tonic convulsions and fatalities are then recorded to determine the $ED_{50}$ and $LD_{50}$ in the presence of the sound challenge.

In a series of similar experiments, the ratio of the 30 minute $LD_{50}$ without sound to the sound-induced $LD_{50}$ for aminophylline, theophylline and caffeine has been found to be greater than 3 for all three compounds, while strychnine exhibited no significant change in toxicity with sound. U.S. Pat. No. 4,136,182.

sound of 148, and an audiogenic convulsion $ED_{50}$ of 135 mg/kg.

The following table illustrates the bronchodilator activity of representative compounds of the invention and their acute toxicity and audiogenic convulsive properties.

| Compound | | | Histamine Blockade | 30 min $LD_{50}$ | Sound 1 $LD_{50}$ | Audiogenic Convulsant $ED_{50}$ |
|---|---|---|---|---|---|---|
| Compounds in which $R_7$, $R_8$ are tetramethylene | | | | | | |
| $R_3$ | $R_6$ | | | | | |
| H | Piperidino | | 72 | 298 | 298 | 283 |
| H | N—Methyl-1-Piperazinyl | | 91 | 147 | 134 | 134 |
| $CH_3$ | Morpholino | | 61 | 149 | 126 | 90 |
| $CH_3$ | Piperidino | | 38 | 139 | 139 | 125 |
| H | Pyrrolidino | | 86 | 191 | 170 | 150 |
| Compounds in which $R_7$, $R_8$ are 1,3-cyclopentylene | | | | | | |
| $R_3$ | $R_6$ | | | | | |
| $CH_3$ | N—Methyl-1-Piperazinyl | | 97 | 147 | 147 | 147 |
| H | N—Methyl-1-Piperazinyl | | 92 | 175 | 147 | 147 |
| $CH_3$ | Pyrrolidino | | 95 | 85 | 85 | 85 |
| H | Pyrrolidino | | 87 | 136 | 100 | 93 |
| H | Piperidino | | 84 | 108 | 98 | 90 |
| $CH_3$ | Morpholino | | 76 | 86 | 74 | 61 |
| Compounds in which $R_7$, $R_8$ are 1,4-cyclohexylene | | | | | | |
| $R_3$ | $R_6$ | | | | | |
| $CH_3$ | Pyrrolidino | | 55 | 141 | 141 | 141 |
| H | Pyrrolidino | | 66 | 136 | 117 | 117 |
| $CH_3$ | N—Methyl-1-Piperazinyl | | 90 | 147 | 147 | 147 |
| H | N—Methyl-1-Piperazinyl | | 82 | 147 | 147 | 113 |
| H | Morpholino | | 58 | 118 | 85 | 62 |
| Compounds in which $R_7$ is Methyl | | | | | | |
| $R_3$ | $R_8$ | $R_6$ | | | | |
| H | $CH_3$ | Piperidino | 45 | 404 | 404 | 404 |
| H | $CH_3$ | Pyrrolidino | 62 | 277 | 277 | 277 |
| H | $CH_3$ | Morpholino | 46 | 272 | 272 | 272 |
| $CH_3$ | H | Piperidino | 48 | 327 | 327 | 260 |
| $CH_3$ | H | Morpholino | 61 | 228 | 148 | 135 |
| H | H | Pyrrolidino | 43 | 272 | 176 | 141 |
| H | H | N—Methyl-1-Piperazinyl | 39 | 272 | 140 | 116 |
| $CH_3$ | $CH_3$ | Piperidino | 30 | 141 | 141 | 141 |
| Phenyl | H | Morpholino* | 22 | >400 | 30 | 5 |
| Aminophylline* | | | 37 | 352 | 83 | 83 |

*Included for comparison

Various triazolopyridazine compounds have been found to exhibit increased toxicity and lowered convulsive thresholds in such procedures, similar to aminophylline. Other triazolopyridazines which have bronchodilator activity exhibit much less toxic potential for audiogenic seizures. For example, the ratio of $LD_{50}$ without sound to $LD_{50}$ with sound for 6-morpholino-7,8-tetramethylene-s-triazolo[4,3-b]pyridazine was found to be 3.8 while the ratio for 6-morpholino-3-methyl-7,8-tetramethylene-s-triazolo[4,3-b]pyridazine was found to be about 1.18. Surprisingly, some triazolopyridazines have been found to exhibit a significant lowering of audiogenic convulsive threshold without an associated increase in sound-induced deaths, as indicated by a low $ED_{50}$ for audiogenic tonic convulsions in comparison to the $LD_{50}$ with sound. The compound 6-morpholino-7-methyl-s-triazolo[4,3-b]pyridazine exhibits desirable bronchodilator activity; and its sound-induced $LD_{50}$ of 280 mg/kg is not greatly below its 30 minute $LD_{50}$ of 327 mg/kg. However, its $ED_{50}$ for audiogenic tonic convulsions is only 45 mg/kg. 6-Morpholino-3,7-dimethyl-s-triazolo[4,3-b]pyridazine in contrast has been found to exhibit much less reduction in convulsive threshold, with an $LD_{50}$ of 228, $LD_{50}$ with

EXAMPLE 59

Histamine Aerosol Exposure

In another procedure, test compounds were administered to guinea pigs by intraperitoneal injection and the guinea pigs were challenged two hours later by exposure to a histamine aerosol. Untreated animals collapse when exposed to the histamine aerosol. In these operations, the animals were observed, and an $ED_{50}$ was calculated as the dosage at which fifty percent of the animals displayed a collapse time greater than the mean collapse time plus two standard deviation units observed with control animals treated with the injection vehicle alone. The $ED_{50}$'s of representative compounds are set out in the following table.

| Compound of Example No. | $ED_{50}$ (mg/kg i.p.) |
|---|---|
| 29 | 5.0 |
| 30 | 1.6 |
| 31 | 4.0 |
| 32 | 2.5 |
| 33 | 1.8 |

-continued

| Compound of Example No. | | ED$_{50}$ (mg/kg i.p.) |
| --- | --- | --- |
| 34 | | 1.3 |
| 38 | | 2.1 |
| 39 | | 2.2 |
| 44 | (dihydrochloride) | 23.8 |
| 45 | | 5.0 |
| 46 | | <5 |
| 47 | (estimated) | 4.95 |
| 51 | | <2.5 |
| 53 | | 36.4 |
| 55 | (estimated) | 7.9 |
| 56 | (estimated) | 5.1 |

The hydrazino pyridazine starting materials can be prepared by known procedures. For example, 3,6-dichloro-4-methylpyridazine heated at reflux with excess hydrazine hydrate (50 percent in water) for 0.3 to 1 hour produces 3-chloro-4-methyl-6-hydrazinopyridazine and 3-chloro-5-methyl-6-hydrazinopyridazine. The isomers can be separated by fractional crystallization using ethanol as a solvent. See, Takahayashi, Pharm. Bull., 5, 229 (1957); Chem. Abstr. 52:6359, Linholter et al., Acta Chem. Scand. 16, 2389 (1962); Chem. Abstr. 59:1632g, Steck et al., J. Amer. Chem. Soc., 76, 4454 (1954) and Horning et al., J. Org. Chem., 20, 707 (1955).

When $R_7$ and $R_8$ are cyclopentylene or cyclohexylene, the dichloro intermediate is conveniently prepared from a 4,5,6,7-tetrahydro-4,7-(methano or ethano)isobenzofuran-1,3-dione. Diels and Alder, Ann., 478, 149 (1930); Ann., 490, 236 (1931). The dione compound is reacted with excess hydrazine hydrate in an exothermic reaction to produce the corresponding hexahydro-5,8-(methano or ethano)phthalazine-1,4-dione. Additional heating at 100°–170° C. for 10–30 minutes may be useful to complete the reaction. The phthalazine-1,4-dione is then reacted with excess phosphorus oxychloride heated at reflux for about 2–4 hours, cooled and the product hydrolyzed by careful addition of ice and water to produce the dichloro intermediate.

In an alternative procedure for preparing substituted triazolopyridazines of Formulae I and II, a 3,6-dihalo-4,5-substituted pyridazine of Formula V

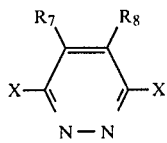
V is reacted with the $R_6$ amine base to prepare a 3-halo pyridazine of Formula VI

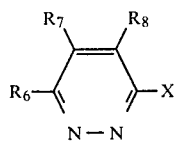
VI

The reaction is conveniently carried out in an inert organic solvent in the presence of an inorganic base, such as sodium carbonate, as a hydrogen halide acceptor.

The resulting 3-halopyridazine is then reacted with a loweralkanoyl hydrazine of Formula VII

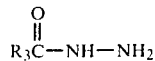
VII to prepare the triazolo pyridazine product. In the above formulae, $R_3$, $R_6$, $R_7$ and $R_8$ have the significance set out above with respect to Formulae I–IV.

The loweralkanoyl hydrazine and 3-halopyridazine are reacted in an inert organic liquid medium such as an alkylene glycol alkyl ether at a temperature of from about 100° C. to about 160° C. The product is recovered and purified by conventional procedures. This procedure is illustrated by the preparation of a preferred compound of the invention, 6-(2-methyl-1-pyrrolidinyl)-7,8-tetramethylene-1,2,4-triazolo[4,3-b]pyridazine, the compound of Example 30.

One gram (0.49 mole) of 3,6-dichloro-4,5-tetramethylene-pyridazine, 78.3 grams (0.738 mole) sodium carbonate, and 500 milliliters of diglyme (diethylene glycol dimethyl ether) were mixed. 46.1 Grams (0.54 mole) of 2-methylpyrrolidine was added slowly with stirring, and the mixture was heated at reflux (134.5° C.) for 72 hours, then cooled to 95° C. 400 Milliliters deionized water was added, and the mixture was cooled to about 25° C. The resulting crystals were separated by filtration, washed with water and dried under reduced pressure to yield 104.0 grams of 3-chloro-6-(2-methyl-1-pyrrolidinyl)-4,5-tetramethylene pyridazine, melting at 134°–136° C.

210 Grams (0.834 mole) of 3-chloro-6-(2-methyl-1-pyrrolidinyl)-4,5-tetramethylene pyridazine, 216 grams (2.92 moles) ethyl formate and 1260 milliliters of ethylene glycol ethyl ether were mixed. Over a 10 minute period, 146.2 grams (2.92 moles) of hydrazine hydrate was added, to form formyl hydrazine in situ. During the addition, the temperature increased from 25° C. to 35° C. The mixture was heated at 100° C. for about 30 minutes, during which time 100 milliliters of ethanol, water and the reaction medium were collected in a Dean Stark trap. The mixture was then heated to reflux at 120° C. for 24 hours, cooled to 95° C., and diluted slowly with about 5 liters of deionized water. The solution was cooled and seeded with product crystals at 60° C., then cooled to 25° C. The crystalline product was collected by filtration, washed with four 500 milliliter portions of deionized water and dried under reduced pressure for about 18 hours at 95° C. 144.3 Grams (67.2% yield) of 6-(2-methyl-1-pyrrolidinyl)-7,8-tetramethylene-1,2,4-triazolo[4,3-b]pyridazine were obtained as a crystalline solid, melting at 144°–145° C.

What is claimed is:

1. A compound corresponding to the formula

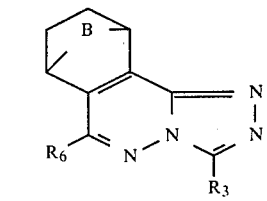

wherein B represents methylene or ethylene; $R_3$ represents hydrogen or loweralkyl; $R_6$ represents amino, loweralkylamino, diloweralkylamino or heterocyclic amino or lower alkyl substituted heterocyclic amino, wherein the heterocyclic moiety forms a 5, 6, or 7 membered ring, having one or two ring nitrogen atoms and zero or one ring sulfur or oxygen atom; or a pharmacologically acceptable salt of said compound.

2. A compound corresponding to the formula

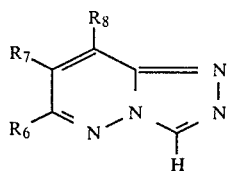

wherein $R_6$ represents N-methyl-1-piperazinyl; and $R_7$ and $R_8$ taken together independently represent polymethylene or substituted polymethylene of 4 methylene units substituted by loweralkyl, or by methano or ethano bridges; or a pharmacologically acceptable salt of said compound.

3. 6-(Hexahydro-4-methyl-1H-1,4-diazepin-1-yl)-3-methyl-7,8-tetramethylene-1,2,4-triazolo[4,3-b]pyridazine.

4. 6-Morpholino-3-methyl-7,8-tetramethylene-1,2,4-triazolo[4,3-b]pyridazine.

5. Compound of claim 1 wherein B is methylene.

6. Compound of claim 5 wherein $R_3$ is hydrogen or loweralkyl and $R_6$ is N-methyl-1-piperazinyl, pyrrolidino, piperidino or morpholino.

7. Compound of claim 6 wherein $R_6$ is N-methyl-1-piperazinyl and $R_3$ is methyl.

8. Compound of claim 6 wherein $R_6$ is pyrrolidino and $R_3$ is methyl.

9. Compound of claim 6 wherein $R_6$ is N-methyl-1-piperazinyl and $R_3$ is hydrogen.

10. Compound of claim 6 wherein $R_6$ is pyrrolidino and $R_3$ is hydrogen.

11. Compound of claim 1 wherein the compound corresponds to the formula

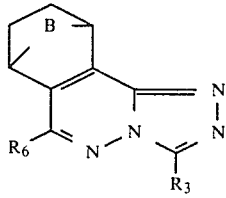

wherein B represents methylene or ethylene and $R_3$ represents hydrogen, methyl, ethyl or isopropyl.

12. Compound of claim 11 wherein B is methylene.

13. Compound of claim 11 wherein B is ethylene.

14. Compound of claim 13 wherein $R_6$ is N-methyl-1-piperazinyl and $R_3$ is methyl.

15. Compound of claim 13 wherein $R_6$ is N-methyl-1-piperazinyl and $R_3$ is hydrogen.

16. Compound of claim 13 wherein $R_6$ is pyrrolidino.

17. A method of alleviating bronchoconstriction in mammals comprising administering to a mammal an effective amount of a composition comprising an effective amount of a compound of the formula

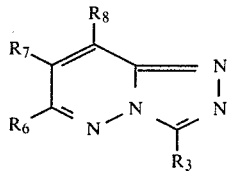

wherein $R_3$ represents hydrogen or lower alkyl; $R_6$ represents amino, loweralkylamino, diloweralkylamino, or heterocyclic amino or lower alkyl substituted heterocyclic amino, wherein the heterocyclic moiety forms a 5, 6, or 7 membered ring, having one or two ring nitrogen atoms and zero or one ring sulfur or oxygen atom; and wherein $R_7$ and $R_8$ taken together independently represent polymethylene or substituted polymethylene of 4 methylene units substituted by loweralkyl, or by methano or ethano bridges; or a pharmacologically acceptable salt of said compound, in admixture with a pharmaceutically-acceptable carrier.

18. Method of claim 17 wherein the compound is administered at a dosage substantially below an audiogenic convulsant dosage.

19. Method of claim 17 wherein the compound has the formula

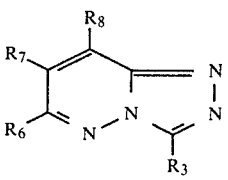

wherein $R_3$ represents hydrogen; $R_6$ represents hexahydro-1H-azepin-1-yl, 2-methyl-1-pyrrolidinyl, piperidino, dimethylamino or pyrrolidino; and $R_7$ and $R_8$ taken together represent tetramethylene; or a pharmacologically acceptable salt of said compound.

20. Method of claim 17 wherein the compound is 6-(2-methyl-1-pyrrolidinyl)-7,8-tetramethylene-1,2,4-triazolo[4,3-b]pyridazine or a pharmacologically acceptable salt thereof.

21. Method of claim 17 wherein the compound is 6-(hexahydro-4-methyl-1H-1,4-diazepin-1-yl)-3-methyl-7,8-tetramethylene-1,2,4-triazolo[4,3-b]pyridazine or a pharmacologically acceptable salt thereof.

22. A bronchodilator composition comprising an effective amount of 6-(hexahydro-4-methyl-1H-1,4-diazepin-1-yl)-3-methyl-7,8-tetramethylene-1,2,4-triazolo[4,3-b]pyridazine or a pharmacologically acceptable salt thereof in admixture with a pharmaceutically acceptable carrier.

* * * * *